(12) United States Patent
Man et al.

(10) Patent No.: US 7,820,697 B2
(45) Date of Patent: *Oct. 26, 2010

(54) COMPOSITIONS AND METHOD FOR REDUCING TNFα LEVELS

(75) Inventors: Hon-Wah Man, Neshanic Station, NJ (US); George W. Muller, Bridgewater, NJ (US)

(73) Assignee: Celgene Corporation, Summit, NJ (US)

( * ) Notice: Subject to any disclaimer, the term of this patent is extended or adjusted under 35 U.S.C. 154(b) by 716 days.

This patent is subject to a terminal disclaimer.

(21) Appl. No.: 11/236,740

(22) Filed: Sep. 28, 2005

(65) Prior Publication Data

US 2006/0030592 A1 Feb. 9, 2006

Related U.S. Application Data

(60) Division of application No. 10/144,560, filed on May 13, 2002, now abandoned, which is a division of application No. 09/942,424, filed on Aug. 31, 2001, now abandoned, which is a continuation of application No. 09/655,571, filed on Sep. 6, 2000, now Pat. No. 6,403,613, which is a continuation-in-part of application No. 09/270,411, filed on Mar. 16, 1999, now abandoned.

(60) Provisional application No. 60/078,180, filed on Mar. 16, 1998.

(51) Int. Cl.
A61K 31/454 (2006.01)
C07D 403/04 (2006.01)

(52) U.S. Cl. ..................... 514/323; 546/200
(58) Field of Classification Search ............... 514/323; 546/200
See application file for complete search history.

(56) References Cited

U.S. PATENT DOCUMENTS

| | | | |
|---|---|---|---|
| 4,590,189 A | 5/1986 | Hiraga et al. | |
| 4,808,402 A | 2/1989 | Leibovich et al. | |
| 4,849,441 A | 7/1989 | Okazaki et al. | |
| 5,385,901 A | 1/1995 | Kaplan et al. | |
| 5,593,990 A | 1/1997 | D'Amato | |
| 5,629,327 A | 5/1997 | D'Amato | |
| 5,635,517 A | 6/1997 | Muller et al. | |
| 5,712,291 A | 1/1998 | D'Amato | |
| 5,798,368 A | 8/1998 | Muller et al. | |
| 5,874,448 A | 2/1999 | Muller et al. | |
| 6,071,948 A | 6/2000 | D'Amato | |
| 6,281,230 B1 | 8/2001 | Muller et al. | |
| 6,316,471 B1 | 11/2001 | Muller et al. | |
| 6,335,349 B1 * | 1/2002 | Muller et al. | 514/323 |
| 6,395,754 B1 | 5/2002 | Muller et al. | |
| 6,403,613 B1 * | 6/2002 | Man et al. | 514/323 |
| 6,458,810 B1 * | 10/2002 | Muller et al. | 514/323 |
| 6,476,052 B1 | 11/2002 | Muller et al. | |
| 6,555,554 B2 | 4/2003 | Muller et al. | |
| 7,041,680 B2 * | 5/2006 | Muller et al. | 514/323 |
| 7,119,106 B2 * | 10/2006 | Muller et al. | 514/323 |
| 7,323,479 B2 * | 1/2008 | Zeldis | 514/323 |

FOREIGN PATENT DOCUMENTS

| | | |
|---|---|---|
| WO | WO 90/08128 | 7/1990 |
| WO | WO 92/18496 | 10/1992 |
| WO | WO 95/01348 | 1/1995 |

OTHER PUBLICATIONS

Jonsson "Chemical structure . . . " CA 78:43185 (1973).*
Corral et al., *The Journal of Immunology*, 380-386 (1999).
Corral et al., *Annals of Reumatic Diseases*, 58(suppl. 1): 1107-1113 (1999).
Corral et al., *Molecular Medicine*, 2(4): 506-515 (1996).
DeVita et al., *Cancer Principles and Practice*, Lippincott, 144-145 (1985).
Gutman et al., CA 126:207258 (1997).
He et al., 206th American Chemical Society National Meeting, *Med. Chem. Abst.* 216 (1993).
Jonsson, *Acta. Pharm. Succica*, 9: 431-436 (1972).
Jonsson, *Acta. Pharm. Succica*, 9: 521-542 (1972).
Joseph et al., *J. Nat'l. Canc. Inst.*, 90: 1648-1653 (1998).
Koch, *Progress in Medicinal Chemistry*, 22: 166-214 (1985).
Miyachi et al., *J. Med. Chem.*, 2858-2865 (1997).
Miyachi et al., *Chem. Pharm. Bull.*, 46(7): 1165-1168 (1998).
Miyachi et al., *Bioorg. Med. Chem. Letters*, 6(19): 2293 (1996).
Moossa et al., *Comprehensive Textbook of Oncology*, Williams & Silkins, 199-202 (1986).
Muller et al., *J. Med. Chem.*, 39(17): 3238-3240 (1996).
Muller et al., *Bioorg. Med. Chem. Letters*, 9: 1625-1630 (1999).
Muller et al., *Bioorg. Med. Chem. Letters*, 8: 2669-2674 (1998).
Nguyen et al., CA 126:324960 (1997).
Shannon et al., *Immunopharmacology*, 35: 203-212 (1997).
Takeuchi et al., *Organic Letters*, 1(10): 1571-1573 (1999).
Udagawa et al., *Angiogenic Agents in Cancer Therapy*, Humana Press Inc., 263-274 (1998).

* cited by examiner

*Primary Examiner*—Celia Chang
(74) *Attorney, Agent, or Firm*—Jones Day

(57) ABSTRACT

1-Oxo- and 1,3-dioxo-2-(2,6-dioxopiperidin-3-yl)isoindolines substituted in the 4- and/or 7-position of the isoindoline ring and optionally further substituted in the 3-position of the 2,6-dioxopiperidine ring reduce the levels of inflammatory cytokines such as TNFα in a mammal. A typical embodiment is 1,3-dioxo-2-(2,6-dioxopiperidin-3-yl)-4-methylisoindoline.

2 Claims, No Drawings

COMPOSITIONS AND METHOD FOR REDUCING TNFα LEVELS

This application is a division of U.S. application Ser. No. 10/144,560, filed May 13, 2002 now abandoned, which is a division of U.S. application Ser. No. 09/942,424, filed Aug. 31, 2001, now abandoned, which is a continuation of U.S. application Ser. No. 09/655,571, filed Sep. 6, 2000, now U.S. Pat. No. 6,403,613, which is a continuation-in-part of U.S. application Ser. No. 09/270,411, filed Mar. 16, 1999, now abandoned, which claims the benefit of U.S. Provisional Application No. 60/078,180 filed on Mar. 16, 1998, all of which are hereby incorporated by reference into this application.

BACKGROUND OF THE INVENTION

Tumor necrosis factor-α, or TNFα, is a cytokine which is released primarily by mononuclear phagocytes in response to a number immunostimulators. It is a key proinflammatory cytokine in the inflammation cascade causing the production and/or release of other cytokines and agents. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., *Nature* 330, 662-664 (1987) and Hinshaw et al., *Circ. Shock* 30, 279-292 (1990)}; cachexia {Dezube et al., *Lancet*, 335 (8690), 662 (1990)} and Adult Respiratory Distress Syndrome (ARDS) where TNFα concentration in excess of 12,000 pg/mL have been detected in pulmonary aspirates from ARDS patients {Millar et al., *Lancet* 2(8665), 712-714 (1989)}. Systemic infusion of recombinant TNFα also resulted in changes typically seen in ARDS {Ferrai-Baliviera et al., *Arch. Surg.* 124(12), 1400-1405 (1989)}.

TNFα appears to be involved in bone resorption diseases, including arthritis. When activated, leukocytes will produce bone-resorption, an activity to which the data suggest TNFα contributes. {Bertolini et al., *Nature* 319, 516-518 (1986) and Johnson et al., *Endocrinology* 124(3), 1424-1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {*Calci. Tissue Int.* (US) 46(Suppl.), S3-10 (1990)}. In Graft versus Host Reaction, increased serum TNFα levels have been associated with major complication following acute allogenic bone marrow transplants {Holler et al., *Blood*, 75(4), 1011-1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., *N. Engl. J. Med.* 320(24), 1586-1591 (1989)}.

Macrophage-induced angiogenesis is known to be mediated by TNFα. Leibovich et al. {*Nature*, 329, 630-632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., *Brit. J Cancer*, (1955) 72, 339-343, and Koch, *Progress in Medicinal Chemistry*, 22, 166-242 (1985)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., *Nature*, 344, 245-247 (1990)}. High levels of TNFα production (in the serum and in isolated macrophages) have been demonstrated in animal models of silica and asbestos induced fibrosis {Bissonnette et al., *Inflammation* 13(3), 329-339 (1989)}. Alveolar macrophages from pulmonary sarcoidosis patients have also been found to spontaneously release massive quantities of TNFα as compared with macrophages from normal donors {Baughman et al., *J Lab. Clin. Med.* 115(1), 36-42 (1990)}.

TNFα is also implicated in the inflammatory response which follows reperfusion, called reperfusion injury, and is a major cause of tissue damage after loss of blood flow {Vedder et al., *PNAS* 87, 2643-2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., *J. Cell Biol.* 107, 1269-1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135(1), 121-132 (1989)}.

TNFα blockage with monoclonal anti-TNFα antibodies has been shown to be beneficial in rheumatoid arthritis {Elliot et al., *Int. J. Pharmac.* 1995 17(2), 141-145}. High levels of TNFα are associated with Crohn's disease {von Dullemen et al., *Gastroenterology*, 1995 109(1), 129-135} and clinical benefit has been achieved with TNFα antibody treatment.

Moreover, it now is known that TNFα is a potent activator of retrovirus replication including activation of HIV-1. {Duh et al., *Proc. Nat. Acad. Sci.* 86, 5974-5978 (1989); Poll et al., *Proc. Nat. Acad. Sci.* 87, 782-785 (1990); Monto et al., *Blood* 79, 2670 (1990); Clouse et al., *J. Immunol.* 142, 431-438 (1989); Poll et al., *AIDS Res. Hum. Retrovirus*, 191-197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad. Sci.,* 87, 782-784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., *PNAS* 86 2336-2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365-2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336-2340 (1989)}. TNFα in AIDS associated cachexia is suggested by elevated serum TNFα and high levels of spontaneous TNFα production in peripheral blood monocytes from patients {Wright et al, *J. Immunol.* 141(1), 99-104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227-29). NFκB has been implicated as a transcriptional activator in a variety of disease and inflammatory states and is thought to regulate cytokine levels including but not limited to TNFα and also to be an activator of HIV transcription (Dbaibo, et al., *J. Biol. Chem.* 1993, 17762-66; Duh et al., *Proc. Natl. Acad. Sci.* 1989, 86, 5974-78; Bachelerie et al., *Nature* 1991, 350, 709-12; Boswas et al., *J Acquired Immune Deficiency Syndrome* 1993, 6, 778-786; Suzuki et al., *Biochem. And Biophys. Res. Comm.* 1993, 193, 277-83; Suzuki et al., *Biochem. And Biophys. Res Comm.* 1992, 189, 1709-15; Suzuki et al., *Biochem. Mol. Bio. Int.* 1993, 31(4), 693-700; Shakhov et al., *Proc. Natl. Acad. Sci. USA* 1990, 171, 35-47; and Staal et al., *Proc. Natl. Acad. Sci. USA* 1990, 87, 9943-47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteo-arthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future,* 17(9), 799-807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle. Phosphodiesterases control the level of cAMP through hydrolysis and inhibitors of phosphodiesterases have been shown to increase cAMP levels.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470-474 (1985); WO 92/113 83}.

DETAILED DESCRIPTION

The present invention is based on the discovery that certain classes of non-polypeptide compounds more fully described herein decrease the levels of TNFα, increase cAMP levels, and inhibit inflammatory cytokines. The present invention thus relates to 1-oxo- and 1,3-dioxo-2-(2,6-dioxopiperidin-3-yl)isoindolines substituted in the 4-position of the isoindoline ring and optionally further substituted in the 3-position of the 2,6-dioxopiperidine ring, the method of reducing levels of tumor necrosis factor α and other inflammatory cytokines in a mammal through the administration of such derivatives, and pharmaceutical compositions containing such derivatives.

In particular, the invention pertains to
(a) a 2-(2,6-dioxopiperidin-3-yl)-isoindoline of the formula:

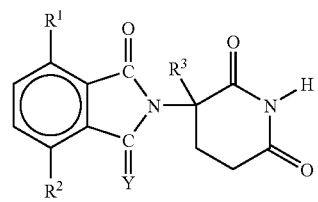

in which
Y is oxygen or $H_2$,
a first of $R^1$ and $R^2$ is halo, alkyl, alkoxy, alkylamino, dialkylamino, cyano, or carbamoyl,
the second of $R^1$ and $R^2$, independently of the first, is hydrogen, halo, alkyl, alkoxy, alkylamino, dialkylamino, cyano, or carbamoyl, and
$R^3$ is hydrogen, alkyl, or benzyl, and (b) the acid addition salts of said 2-(2,6-dioxopiperidin-3-yl)-isoindolines which contain a nitrogen atom capable of being protonated.

Unless otherwise defined, the term alkyl denotes a univalent saturated branched or straight hydrocarbon chain containing from 1 to 4 carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy.

Halo includes bromo, chloro, fluoro, and iodo.

The compounds of Formula I are used, under the supervision of qualified professionals, to inhibit the undesirable effects of TNFα and other inflammatory cytokines including the interleukins IL-1, IL-6, and IL-12. The compounds can be administered orally, rectally, or parenterally, alone or in combination with other therapeutic agents including antibiotics, steroids, chemotherapeutic agents, etc., to a mammal in need of treatment; e.g. in the treatment of cancers, rheumatoid arthritis, inflammatory bowel disease, muscular dystrophy, Crohn's disease, etc.

The compounds of the present invention also can be used topically in the treatment or prophylaxis of disease states mediated or exacerbated by excessive TNFα production, respectively, such as viral infections, such as those caused by the herpes viruses, or viral conjunctivitis, psoriasis, atopic dermatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The compounds of Formula I are readily prepared through a number of routes. In a first embodiment, an anhydride or lactone is allowed to react with a 3-amino-2,6-dioxopiperidine:

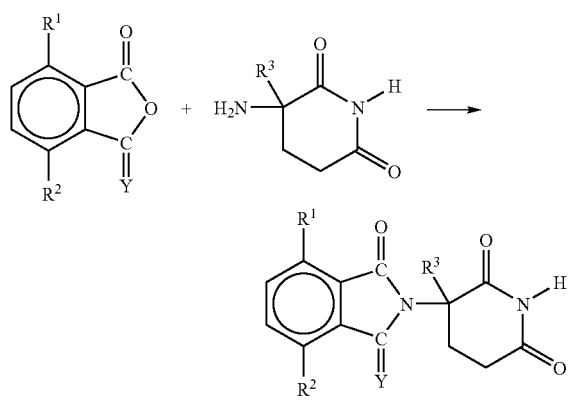

In the foregoing reactions, each of $R^1$, $R^2$, $R^3$, and Y are as defined above.

The 3-amino-2,6-dioxopiperidine can be obtained from the corresponding glutamic acid anhydride through conventional amidation or from the cyclization of appropriate glutamine derivatives.

The compounds in which Y is $H_2$ alternatively can be obtained from a disubstituted benzoate intermediate according to the following reactions:

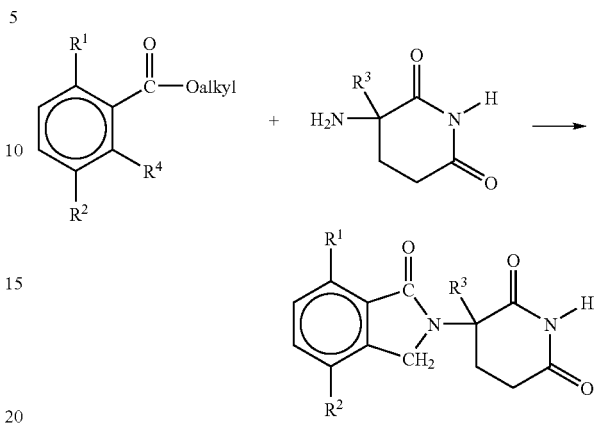

in which $R^4$ is CHO or $CH_2Br$ in the presence of an acid acceptor such as dimethylaminopyridine or triethylamine.

The disubstituted benzoate intermediates are known or can be obtained though conventional processes. For example, a lower alkyl ester of a 3,6-disubstituted ortho-toluic acid is brominated with N-bromosuccinimide under the influence of light to yield the lower alkyl 2-(bromomethyl)-3,6-disubstitutedbenzoate.

Alternatively, a dialdehyde is allowed to react with 2,6-dioxopiperidin-3-ammonium chloride to obtain the compounds of Formula I in which Y is $H_2$:

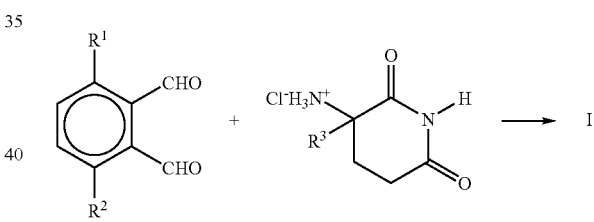

Finally, a dialdehyde is allowed to react with glutamine and the resulting 2-(1-oxoisoindolin-2-yl)glutaric acid then cyclized to yield a 4,7-disubstituted 1-oxo-2-(2,6-dioxopiperidin-3-yl)-isoindoline of Formula I in which Y is $H_2$:

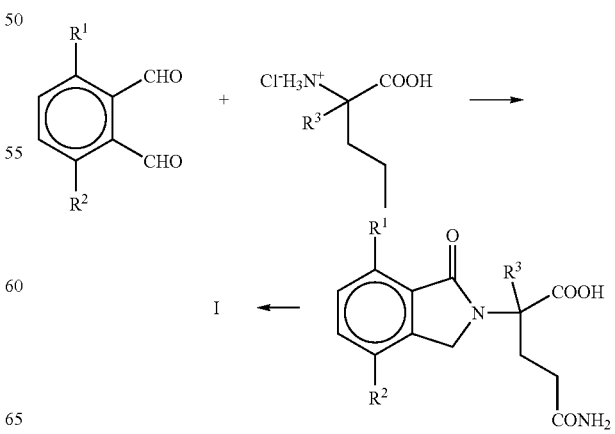

The carbon atom to which $R^3$ is bound in the compounds of Formula I constitutes a center of chirality, thereby giving rise to optical isomers:

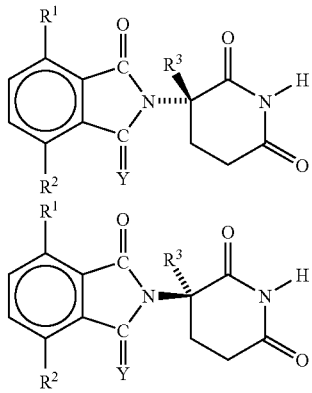

Both the racemates of these isomers and the individual isomers themselves, as well as diastereomers when a second chiral center is present, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid or base, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The present invention also pertains to the physiologically acceptable non-toxic acid addition salts of the compound of Formula I which contain a group capable of being protonated; e.g., amino. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Particularly preferred compounds include 1,3-dioxo-2-(2,6-dioxopiperidin-3-yl)-4-methylisoindoline, 1,3-dioxo-2-(2,6-dioxopiperidin-3-yl)-4-methylisoindoline, 1,3-dioxo-2-(2,6-dioxo-3-methylpiperidin-3-yl)-4-methylisoindoline, 1,3-dioxo-2-(2,6-dioxoopiperidin-3-yl)-4,7-dimethylisoindoline, 1-oxo-2-(2,6-dioxo-3-methylpiperidin-3-yl)-4-ethylisoindoline, 1-oxo-2-(2,6-dioxo-3-methylpiperidin-3-yl)-4-methylisoindoline, 1-oxo-2-(2,6-dioxo-3-methylpiperidin-3-yl)-7-ethylisoindoline, 1-oxo-2-(2,6-dioxo-3-methylpiperidin-3-yl)-7-methylisoindoline, 1-oxo-2-(2,6-dioxopiperidin-3-yl)-4-propylisoindoline, 1,3-dioxo-2-(2,6-dioxopiperidin-3-yl)-4-chloroisoindoline, 1,3-dioxo-2-(2,6-dioxopiperidin-3-yl)-4-carbamoylisoindoline, 1,3-dioxo-2-(2,6-dioxopiperidin-3-yl)-4-methoxyisoindoline, 1-oxo-2-(2,6-dioxoopiperidin-3-yl)-4,7-dimethylisoindoline, 1-oxo-2-(2,6-dioxoopiperidin-3-yl)-4-methyl-7-ethylisoindoline, and 1-oxo-2-(2,6-dioxopiperidin-3-yl)-4,7-diethoxyisoindoline. Of these, 1,3-dioxo-2-(2,6-dioxopiperidin-3-yl)-4-methylisoindoline, 1,3-dioxo-2-(2,6-dioxopiperidin-3-yl)-4,7-dimethylisoindoline, 1-oxo-2-(2,6-dioxopiperidin-3-yl)-4-methylisoindoline, and 1 oxo-2-(2,6-dioxopiperidin-3-yl)-4,7-dimethylisoindoline are particularly preferred.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formulas I associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Enzyme-linked immunosorbent assays for TNFα can be performed in a conventional manner. PBMC is isolated from normal donors by Ficoll-Hypaque density centrifugation. Cells are cultured in RPMI supplemented with 10% AB+ serum, 2 mM L-glutamine, 100 U/mL penicillin, and 100 mg/mL streptomycin. Drugs are dissolved in dimethylsulfoxide (Sigma Chemical) and further dilutions are done in supplemented RPMI. The final dimethylsulfoxide concentration in the presence or absence of drug in the PBMC suspensions is 0.25 wt %. Drugs are assayed at half-log dilutions starting at 50 mg/mL. Drugs are added to PBMC ($10^6$ cells/mL) in 96 wells plates one hour before the addition of LPS. PBMC ($10^6$ cells/mL) in the presence or absence of drug are stimulated by treatment with 1 mg/mL of LPS from *Salmonella minnesota* R595 (List Biological Labs, Campbell, Calif.). Cells are then incubated at 37° C. for 18-20 hours. Supernatants are harvested and assayed immediately for TNFα levels or kept frozen at −70° C. (for not more than 4 days) until assayed. The concentration of TNFα in the supernatant is determined by human TNFα ELISA kits (ENDOGEN, Boston, Mass.) according to the manufacturer's directions.

The following examples will serve to further typify the nature of this invention but should not be construed as a limitation in the scope thereof, which scope is defined solely by the appended claims.

EXAMPLE 1

2-(2,6-Dioxopiperid-3-yl)-4-methylisoindoline-1,3-dione

A stirred solution of 3-methylphthalic anhydride (2.96 g, 18.2 mmol), 3-aminopiperidine-2,6-dione hydrogen chloride (3.00 g, 18.2 mmol) and sodium acetate (1.57 g, 19.1 mmol) in acetic acid (30 mL) was heated at reflux for 23 hours. The solvent was removed in vacuo to give a solid which was stirred with water (40 mL) for 1 hour, filtered, washed with water (30 mL), and then heated with decolorizing charcoal (1 g) in acetone (2 L) at reflux temperature for 30 min. The suspension was filtered through a pad of Celite to give a clear solution. The solvent of filtrate was removed in vacuo to give 2-(2,6-dioxopiperid-3-yl)-4-methylisoindoline-1,3-dione as a white solid (4.08 g, 82% yield)-mp 290.0-292.0° C.; $^1$H NMR (DMSO-d6); δ 2.03-2.09 (m, 1H, CHH), 2.50-2.60 (m, 2H, CH$_2$), 2.63 (s, 3H, CH$_3$), 2.83-2.95 (m, 1H, CHH), 5.13 (dd, J=5.4, 12.3 Hz, 1H, NCH), 7.65-7.79 (m, 3H, Ar), 11.13 (br s, 1H, NH); $^{13}$C NMR (DMSO-d6) δ 17.04, 21.99, 30.93, 48.76, 121.05, 127.89, 131.63, 134.37, 136.91, 137.61, 167.04, 167.83, 169.87, 172.74; Anal Calcd for $C_{14}H_{12}N_2O_4$: C, 61.76; H, 4.44; N, 10.29. Found: C, 61.68; H, 4.37; N, 10.17.

EXAMPLE 2

By substituting equivalent amounts of 3-ethylphthalic anhydride, 3-fluorophthalic anhydride, 3-chlorophthalic anhydride, 3-carbamoylphthalic anhydride, and 3-methoxyphthalic anhydride in the procedure of Example 1, there are respectively obtained 1,3-dioxo-2-(2,6-dioxopiperidin-3-yl)-4-ethylisoindoline, 1,3-dioxo-2-(2,6-dioxopiperidin-3-yl)-4-fluoroisoindoline, 1,3-dioxo-2-(2,6-dioxopiperidin-3-yl)-4-chloroisoindoline, 1,3'-dioxo-2-(2,6-dioxopiperidin-3-yl)-4-carbamoylisoindoline, 1,3-dioxo-2-(2,6-dioxopiperidin-3-yl)-4-methoxyisoindoline.

EXAMPLE 3

By substituting equivalent amounts of 3-amino-3-methylpiperidine-2,6-dione hydrogen chloride for 3-aminopiperidine-2,6-dione hydrogen chloride in the procedure of Example 1, 1,3-dioxo-2-(2,6-dioxo-3-methylpiperidin-3-yl)-4-methylisoindoline is obtained.

EXAMPLE 4

1-Oxo-2-(2,6-dioxopiperidin-3-yl)-4-methylisoindoline

A mixture of 16.25 g of 2,6-dioxopiperidin-3-ammonium chloride, and 30.1 g of methyl 2-bromomethyl-3-methylbenzoate, and 12.5 g of triethylamine in 100 mL of dimethylformamide is stirred at room temperature for 15 hours. The mixture is then concentrated in vacuo and the residue mixed with methylene chloride and water. The aqueous layer is separated and back-extracted with methylene chloride. The combined methylene chloride solutions are dried over magnesium sulfate and concentrated in vacuo to give 1-oxo-2-(2,6-dioxopiperidin-3-yl)-4-methylisoindoline.

In a similar fashion 1-oxo-2-(2,6-dioxopiperidin-3-yl)-4,7-dimethylisoindoline, 1-oxo-2-(2,6-dioxopiperidin-3-yl)-4-ethylisoindoline, and 1-oxo-2-(2,6-dioxopiperidin-3-yl)-4-methoxyisoindoline are obtained by substituting equivalent amounts of methyl 2-bromomethyl-3,6-dimethylbenzoate, methyl 2-bromomethyl-3-ethylbenzoate, and methyl 2-bromomethyl-3-methoxybenzoate, respectively, for methyl 2-bromomethyl-3-methylbenzoate.

EXAMPLE 5

2-(2,6-Dioxopiperidin-3-yl)-4,7-dimethylisoindoline-1,3-dione 2-(2,6-Dioxopiperid-3-yl)-4,7-dimethylisoindoline-1,3-dione was prepared by the procedure of Example 1 from 3,6-dimethylphthalic anhydride (220 mg, 1.25 mmol), 3-aminopiperidine-2,6-dione hydrogen chloride (204 mg, 1.24 mmol) and sodium acetate (110 mg, 1.34 mmol) in acetic acid (10 mL). The product is a white solid (200 mg, 56% yield): mp 263.0-265.0° C.; $^1$H-NMR (DMSO-d$_6$) δ 2.01-2.07 (m, 1H, CHH), 2.50-2.89 (m, 9H, CH$_3$, CHH, CH$_2$), 5.10 (dd, J=5.1, 12.4 Hz, 1H, NCH), 7.52 (s, 2H, Ar), 11.12 (br s, 1H, NH); $^{13}$C NMR (DMSO-d$_6$) δ 16.82, 22.02, 30.97, 48.59, 128.01, 135.04, 136.58, 167.68, 169.98, 172.83.

EXAMPLE 6

2-(2,6-Dioxo(3-piperidyl))-4-ethylisoindoline-1,3-dione 2-(2,6-Dioxo(3-piperidyl))-4-ethylisoindoline-1,3-dione was prepared by the procedure of Example 1 from 3-ethylphthalic anhydride (0.860 g, 4.89 mmol), 3-aminopiperidine-2,6-dione hydrogen chloride (0.803 g, 4.88 mmol) and sodium acetate (0.420 g, 5.12 mmol) in acetic acid (10 mL). The product was a white solid (1.06 g, 76% yield); mp, 235.0-236.5° C.; $^1$H NMR (DMSO-d$_6$) δ 1.22 (t, J=7.4 Hz, 3H, CH$_3$), 2.04-2.10 (m, 1H, CHH), 2.47-2.63 (m, 2H, CH$_2$), 2.83-2.98 (m, 1H, CHH), 3.07 (q, J=7.5 Hz, 2H, CH$_2$), 5.13 (dd, J=5.4, 12.5 Hz, 1H, NCH), 7.70-7.82 (m, 3H, Ar), 11.13 (br s, 1H, NH); $^{13}$C NMR (DMSO-d$_6$) δ 14.84, 21.95, 23.69, 30.90, 48.77, 121.09, 127.26, 131.76, 134.63, 135.39, 143.87, 166.99, 167.58, 169.85, 172.72; Anal Calcd for $C_{15}H_{14}N_2O_4$: C, 62.93; H, 4.93; N, 9.79. Found: C, 62.74; H, 4.84; N, 9.54.

EXAMPLE 7

4-Methoxy-2-(2,6-dioxo(3-piperidyl))isoindoline-1,3-dione

4-Methoxy-2-(2,6-dioxo(3-piperidyl))isoindoline-1,3-dione was prepared by the procedure of Example 1 from 3-methoxyphthalic anhydride (1.0 g, 5.6 mmol) {Rao. A. V. R. et al, Indian J. Chem. 1981, 20 (B), 248}, 3-aminopiperidine-2,6-dione hydrogen chloride (0.92 g, 5.6 mmol) and sodium acetate (0.48 g, 6.0 mmol) in acetic acid (20 mL). The product was a white solid (0.44 g, 27% yield), mp, 281.5-282.5° C.; $^1$H NMR (DMSO-d$_6$) δ 2.00-2.08 (m, 1H, CHH), 2.56-2.62 (m, 2H, CH$_2$), 2.82-2.91 (m, 1H, CHH), 3.97 (s, 3H, CH$_3$), 5.08 (dd, J=5.3, 12.8 Hz, 1H, NCH), 7.46 (d, J=7.2 Hz, 1H, Ar), 7.52 (d, J=8.5 Hz, 1H, Ar), 7.84 (d, J=7.8 Hz, 1H, Ar), 11.10 (br s, 1H, NH); $^{13}$C NMR (DMSO-d$_6$) δ 21.97, 30.92, 48.73, 56.33, 115.24, 116.11, 119.01, 133.19, 137.15, 156.49, 165.37, 166.84, 169.94, 172.79; Anal Calcd for $C_{14}H_{12}N_2O_5$: C, 58.33; H, 4.20; N, 9.72. Found: C, 58.23; H, 3.90; N, 9.53.

EXAMPLE 8

4-Dimethylamino-2-(2,6-dioxo(3-piperidyl))isoindoline-1,3-dione

4-Dimethylamino-2-(2,6-dioxo(3-piperidyl))isoindoline-1,3-dione was prepared by the procedure of Example 1 from 3-dimethylaminophthalic anhydride (1.34 g, 7.0 mmol), 3-aminopiperidine-2,6-dione hydrogen chloride (1.15 g, 7.0 mmol) and sodium acetate (0.60 g, 7.3 mmol) in acetic acid (20 mL). The product was a yellow solid (1.59 g, 75% yield); mp, 214.5-216.5° C.; $^1$H NMR (DMSO-$d_6$) δ 1.98-2.09 (m, 1H, CHH), 2.49-2.62 (m, 2H, CH$_2$), 2.81-2.95 (m, 1H, CHH), 3.04 (s, 6H, CH$_3$), 5.08 (dd, J=5.5, 12.7 Hz, 1H, NCH), 7.23 (d, J=6.6 Hz, 1H, Ar), 7.26 (d, J=8.1 Hz, 1H, Ar), 7.63 (dd, J=6.9, 8.6 Hz, 1H, Ar), 11.09 (br s, 1H, NH); $^{13}$C NMR (DMSO-$d_6$) δ 22.10, 30.96, 42.95, 48.77, 112.99, 113.41, 122.59, 133.90, 135.22, 149.88, 166.29, 167.13, 170.06, 172.83; Anal Calcd for $C_{15}H_{15}N_3O_4$: C, 59.80; H, 5.02; N, 13.95. Found: C, 59.60; H, 4.94; N, 13.80.

EXAMPLE 9

2-(2,6-Dioxo(3-piperidyl))-4-chloroisoindoline 1,3-dione 2-(2,6-Dioxo(3-piperidyl))-4-chloroisoindoline-1,3-dione was prepared by the procedure of Example 1 from 3-chlorophthalic anhydride (0.40 g, 2.2 mmol), 3-aminopiperidine-2,6-dione hydrogen chloride (0.36 g, 2.2 mmol) and sodium acetate (0.19 g, 2.4 mmol) in acetic acid (10 mL). The product was a white solid (0.44 g, 69% yield); mp, 290.0-291.5° C.; $^1$H NMR (DMSO-$d_6$) δ 2.05-2.11 (m, 1H, CHH), 2.49-2.64 (m, 2H, CH$_2$), 2.64-2.92 (m, 1H, CHH), 5.17 (dd, J=5.2, 12.7 Hz, 1H, NCH), 7.86-7.94 (m, 3H, Ar), 11.17 (br s, 1H, NH); $^{13}$C NMR (DMSO-$d_6$) δ 21.83, 30.91, 49.12, 122.41, 126.94, 129.84, 133.52, 136.11, 136.39, 164.77, 165.76, 169.73, 172.77; Anal Calcd for $C_{13}H_9N_2O_4Cl$: C, 53.35; H, 3.10; N, 9.57; Cl, 12.11. Found: C, 53.37; H, 2.94; N, 9.30, Cl, 11.97.

EXAMPLE 10

4-Methyl-2-(2,6-dioxo-3-methyl-(3-piperidyl))isoindoline-1,3-dione

4-Methyl-2-(2,6-dioxo-3-methyl-(3-piperidyl))isoindoline-0,1,3-dione was prepared by the procedure of Example 1 from 3-methylphthalic anhydride (0.27 g, 1.7 mmol), 3-amino-3-methylpiperidine-2,6-dione hydrogen chloride (0.30 g, 1.7 mmol) and sodium acetate (0.15 g, 1.8 mmol) in acetic acid (10 mL). The product was a white solid (0.13 g, 27% yield); mp, 248.0-250.0° C.; $^1$H NMR (DMSO-$d_6$) δ 1.89 (s, 3H, CH$_3$), 2.01-2.08 (m, 1H, CHH), 2.49-2.70 (m, 3H, CHH, CH$_2$), 2.55 (s, 3H, CH$_3$), 7.62-7.74 (m, 3H, Ar), 10.99 (br s, 1H, NH); $^{13}$C NMR (DMSO-$d_6$) δ 17.0, 21.0, 28.6, 29.1, 58.6, 120.7, 127.5, 131.5, 134.2, 136.8, 137.2, 167.7, 168.6, 172.1, 172.3; Anal. Calcd. for $C_{15}H_{14}N_2O_4$+ 0.3H$_2$O: C, 61.77; H, 5.05; N, 9.60. Found: C, 62.05; H, 4.94; N, 9.20.

EXAMPLE 11

Tablets, each containing 50 mg of 1-oxo-2-(2,6-dioxopiperidin-3-yl)-4-methylisoindoline, can be prepared in the following manner:

| Constituents (for 1000 tablets) | |
|---|---|
| 1-oxo-2-(2,6-dioxo-piperidin-3-yl)-4-methyl-isoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 12

Gelatin dry-filled capsules, each containing 100 mg of 1,3-dioxo-2-(2,6-dioxopiperidin-3-yl)-4-methylisoindoline, can be prepared in the following manner:

| Composition (for 1000 capsules) | |
|---|---|
| 1,3-dioxo-2-(2,6-dioxo-piperidin-3-yl)-4-methyl-isoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1,3-dioxo-2-(2,6-dioxopiperidin-3-yl)-4-methylisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 13

A 0.2% injection or infusion solution can be prepared, for example, in the following manner:

| | |
|---|---|
| 1,3-dioxo-2-(2,6-dioxopiperidin-3-yl)-4,7-dimethylisoindoline | 5.0 g |
| sodium chloride | 22.5 g |
| phosphate buffer pH 7.4 | 300.0 g |
| demineralized water | to 2500.0 mL |

1-Dioxo-2-(2,6-dioxopiperidin-3-yl)-4,7-dimethylisoindoline is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

What is claimed is:

1. A pharmaceutical composition comprising a racemic mixture of compound of the following formula:

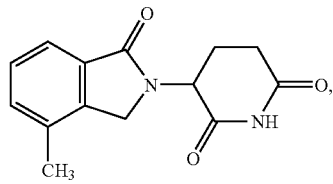

or an acid addition salt thereof, and a pharmaceutically acceptable carrier, diluent, or excipient.

2. The pharmaceutical composition of claim 1, wherein the composition is suitable for oral or parenteral administration.

* * * * *